United States Patent [19]

Hillsman

[11] 3,991,304

[45] Nov. 9, 1976

[54] RESPIRATORY BIOFEEDBACK AND PERFORMANCE EVALUATION SYSTEM

[76] Inventor: Deane Hillsman, 870 El Chorro Way, Sacramento, Calif. 95825

[22] Filed: May 19, 1975

[21] Appl. No.: 578,972

[52] U.S. Cl. .......................... 235/151.34; 179/1 SP; 128/2.08
[51] Int. Cl.² ...................... A61B 5/08; G09B 19/00
[58] Field of Search ............ 235/151.34, 151.3, 150; 128/2.08, 2.07; 340/324 AD; 179/1 SA, 1 SB, 1 SM, 1 SP

[56] References Cited
UNITED STATES PATENTS

| | | | |
|---|---|---|---|
| 3,387,090 | 6/1968 | Bridges | 179/1 SP |
| 3,857,385 | 12/1974 | Hampi | 128/2.08 |
| 3,881,059 | 4/1975 | Stewart | 179/1 SP |

OTHER PUBLICATIONS

An Instrument for the Accurate Measurement of MEFV Parameters, Philip J. Gulesian, Jr., IEEE Transactions on Bio-Medical Engineering, Sept. 1971, pp. 378–382.
Automated System for Measurement of Mechanics of Breathing, H. Watson, J. Landa, and M. A. Sackner, Medical Instrumentation, vol. 9, No. 1, Jan.–Feb. 1975, pp. 3–10.

*Primary Examiner*—Edward J. Wise
*Attorney, Agent, or Firm*—L. G. Wise

[57] ABSTRACT

A positive biofeedback training system which visually displays desired respiratory parameters along with performance. Suitable respiratory airflow transducer means is used to generate and compare flow signals in real time to the physician-, technician-, or teacher - prescribed desirable performance parameters, thus providing incentives to improve patient or student performance for respiratory maneuvers under varying circumstances. The system includes estimation means to quantitate deficiencies of volumetric, flow, pressure, or timing requirements to the ideal breathing patterns. The system includes methods and a flow signal is integrated to appropriate volume signal with relation to a time base. The system provides for detecting initiation of inspiration and resetting of ideal volumetric respiration pattern; comparing real time flow and volumetric signal with ideal flow and volumetric prescribed patterns, and visually displaying both ideal and real time performance on a suitable display.

This system is particularly adapted for clinic use to establish an ideal breathing pattern under various circumstances and to establish a mechanical prescription for adaptation in home use by a respiratory victim utilizing simpler device means. Appropriate performance deficiency indicators or performance enhancing indicators may be used. Appropriate performance signal recording devices and data analysis devices may be attached.

The system may be further adapted for optimizing breathing device performance, breathing testing performance, and other breathing training and evaluation parameters in normal subjects training to work in unusual environments or for use with musical instrument or voice training or pregnant delivering subjects and the like.

In the preferred embodiments of the invention, prescribed waveforms for inspiration flow, expiration flow, relative timing ratios of inspiration to expiration, etc. are read out of ROMs and compared with sample integrated airflow values from a RAM. A scanning beam rectilinear raster display is employed for converting digital values in real time superimposed patterns.

19 Claims, 16 Drawing Figures

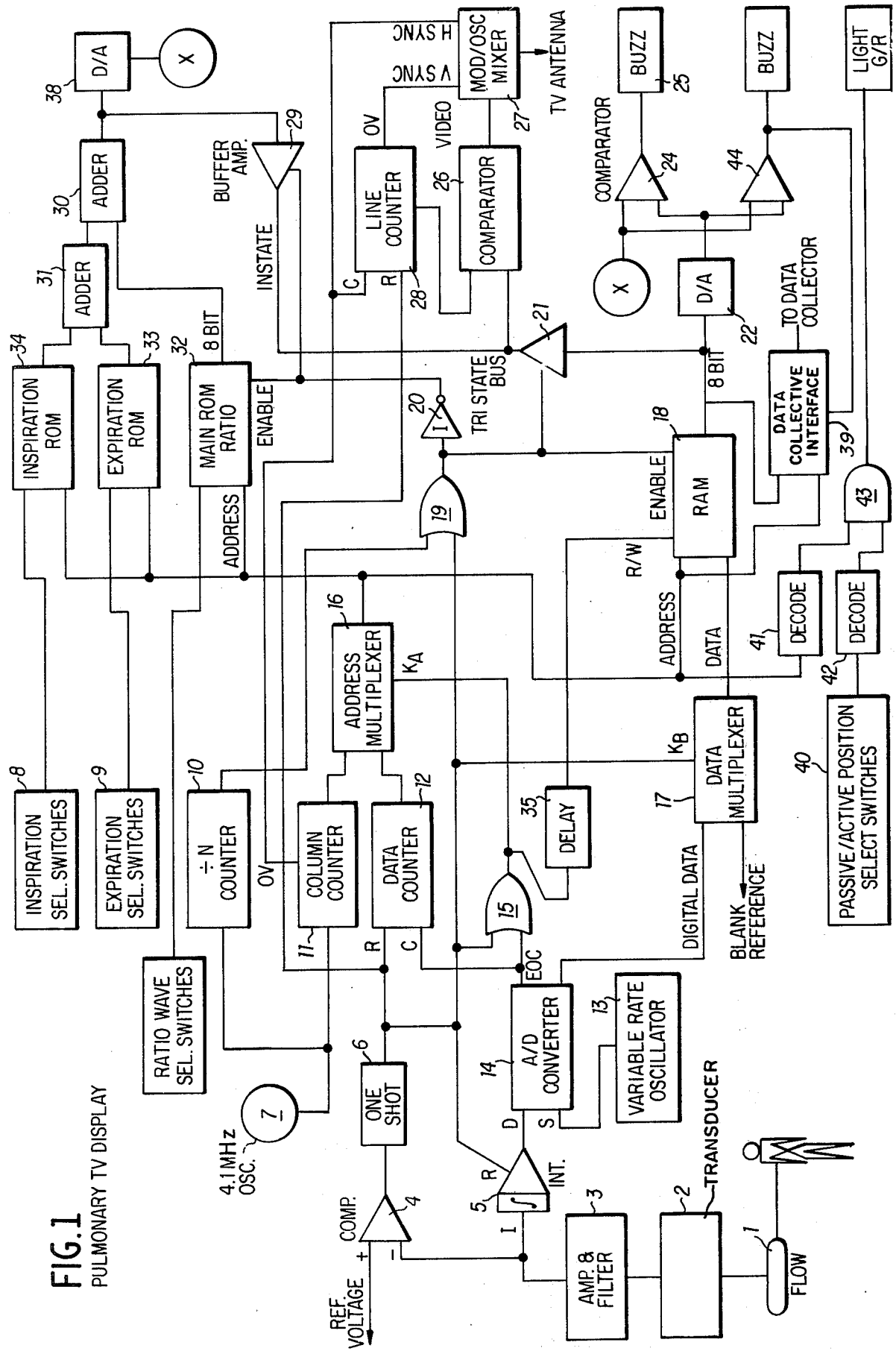
FIG.1 PULMONARY TV DISPLAY

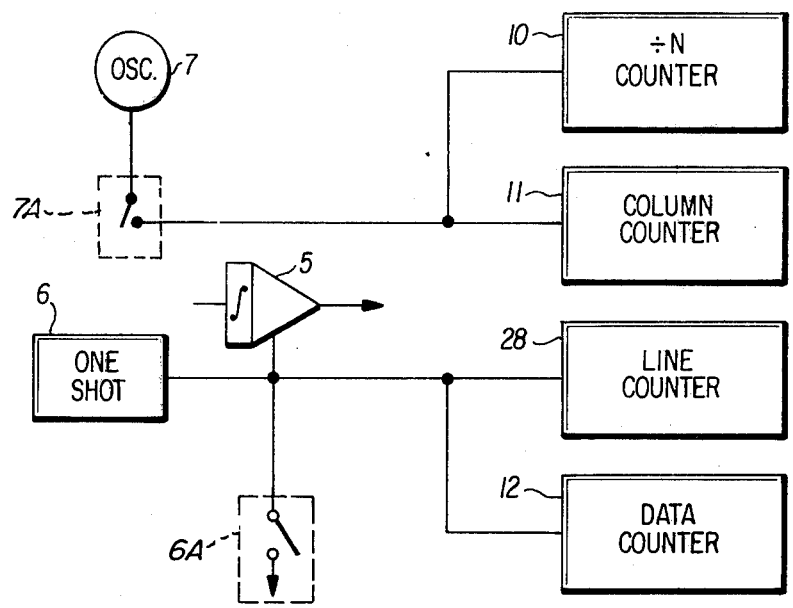
FIG. 1a
FIG. 1b
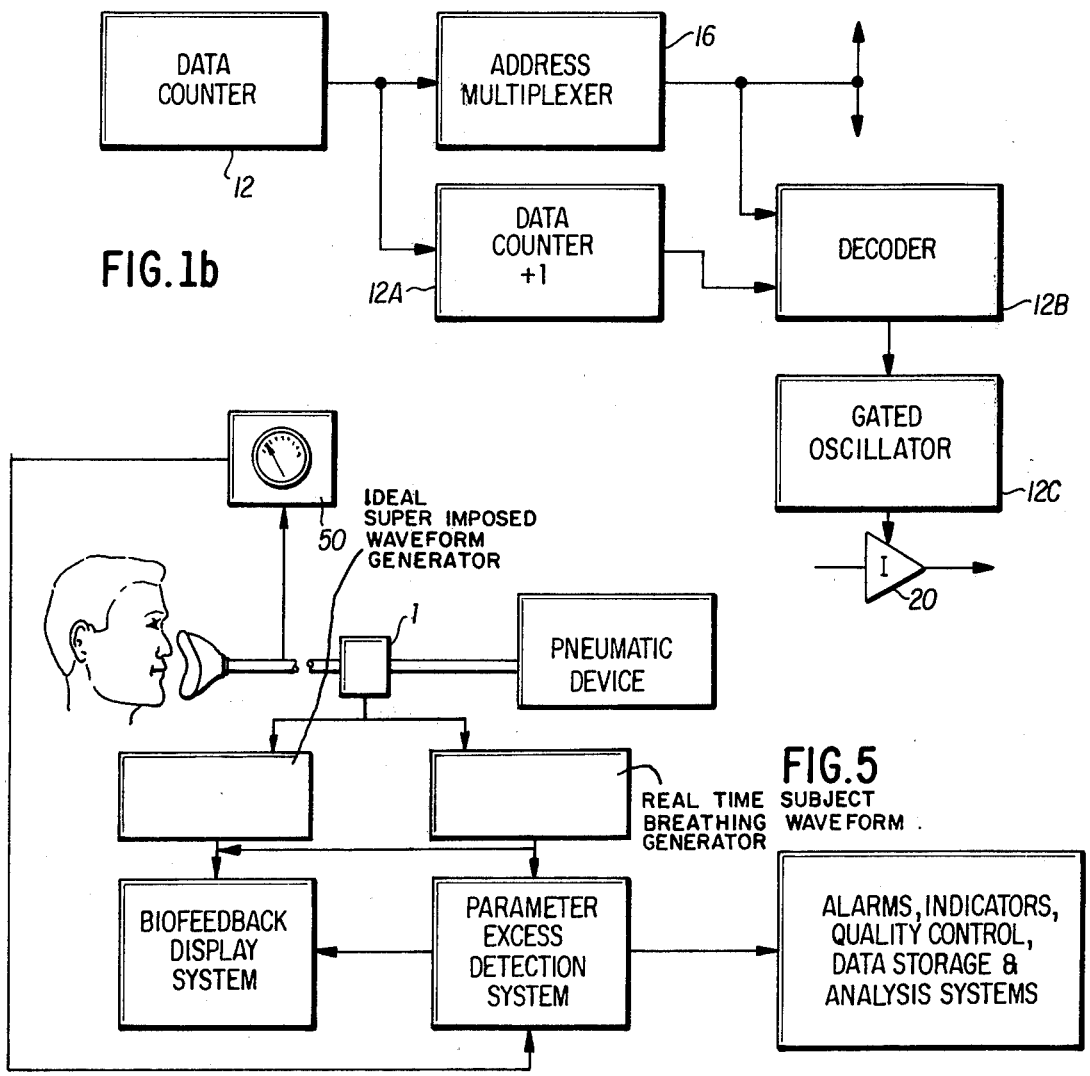
FIG. 5

RESPIRATORY BIOFEEDBACK AND PERFORMANCE EVALUATION SYSTEM

BACKGROUND OF THE INVENTION

This invention relates to improved methods and apparatus for biofeedback and display of respiration performance. In particular, it relates to systems for optimizing air delivery to the lung. Spontaneous breathing, as well as augmented breathing utilizing respiratory assistive devices, may be improved. In addition, this concept includes systems for inhalation therapy treatment for efficient delivery of aerosol and/or dust particles to the lung with optimum individualized breathing patterns.

Breathing patterns are defined by the size of the breath (tidal volume), the number of breaths per minute (respiratory frequency), the time ratio of inspiration to expiration (inspiration/expiration ratio), and the volume/time (flow) waveform patterns within the above noted volume and time constraints. The desirable breathing pattern to combat certain types of health problems may be quite different from the patterns necessary for mechanically assisted breathing, for aerosol/dust delivery to the lungs or for other clinical problems. For example, in problems of diseases generally classified as airway obstructive — such as e.g. asthma, bronchitis or emphysema — there is a need for a slow respiratory rate, long expiratory time ratio, and a relatively large tidal volume and breathing waveform patterns that may be quite unique to the individual. By contrast, the patient with so-called restrictive lung disease, e.g. pulmonary fibrosis, or many other diseases that may cause a loss of lung volume without airway obstructive problems of dominant significance, efficient breathing generally requires smaller tidal volumes, a more rapid respiratory rate, and a more rapid expiratory time ratio, again with breathing wave forms that might be guite unique. Regardless of underlying lung disease, when the patient receives assistive breathing with or without the added requirement for aerosol/-dust delivery to the lungs, other sets of optimized breathing patterns may be needed for the particular patient, above and beyond the pattern requirement for normal spontaneous breathing. In any of the above noted problems, the expiratory phase is desirably "passive", that is, passive recoil of the elastic lung/chest wall structures force the air out of the patient with maximum ease and efficiency, minimum patient energy expenditure, and minimum increases in lung pressure to thereby avoid so-called "dynamic bronchial compression" and further restriction to the airflow passages. However, in many airway obstructive problems, particularly those due to advanced emphysema with an excessively prolonged expiration time, a variable portion of the terminal expiratory phase should be variably "active", that is, utilizing active muscular contracture to force that air out of the lungs.

The normal respiration rate for humans is about 12 to 15 cycles per minute, with an inspiration:expiration time ratio of about 1:1.4. A typical 70 Kg adult human has a tidal volume of about 500 cc. A lifetime of experience combined with instinctive breathing patterns tend to provide respiration having characteristics that are ingrained in the persons individual physiology. When a person encounters an abnormal breathing situation with different mehanical contraints for efficient breathing, it may require extensive training to modify his established habits and instinctive rhythms.

Adapting to an abnormal respiratory condition frequently requires the subject to adopt a slower respiratory rate, for instance, a rate reduction from rapid gasping breathing of perhaps 25 cycles/minute to normal respiratory rates, or sometimes even less than 12 cycles/minute, particularly for diseased lungs with an "airway obstructive" disease. The expiration time is often longer, resulting in a lower inspiration: expiration ratio, e.g.—1:2 to 1:3.

In order to maintain adequate oxygen supply and carbon dioxide elimination, the tidal volume is increased to compensate for the slower cycle rate. These patterns may require particularly extensive training. In addition to training for ordinary quiet breathing, where the person is at rest, it is often desired to train for an exertion pattern to permit increased active physical activity. Special problems in respiratory control are encountered in suppressing a "panic attack", which may result from a patient's coughing spasm or excitement, which results in rapid gasping breathing which will interfere with pulmonary functions.

Widespread emphysema is a major health problem, and this invention is intended for use in training and treatment of persons suffering from this disorder. Emphysema can particularly cause dynamic bronchial compression, which calls for specially prescribed respiration.

For chronic emphysema patients learning a prescribed respiration cycle, it is mandatory to achieve the volume of air necessary to sustain life. In such cases, the training permits the patient to learn an overall breathing cycle which consumes minimum energy and reduces the distress of shortness of breath.

Shortness of breath, dyspnea, may thereby be treated in diseased patients with a variety of disorders. Dyspneic patients having difficult or labored respiration may be trained to respond to effective patterns.

Teaching a normal person dynamic breath control, with musical voice or instrument breathing control or improving respiratory functions for underwater diving, mountaineering or various atheletic activities, can also employ breathing training systems.

It should be apparent from the above, that breathing patterns must be highly individualized for the particular problem. Considering that desirable breathing patterns may be very different from the pathologic breathing patterns, and that the prescribed breathing patterns may be difficult for a patient to learn, it should also be apparent that there is a need to quantitate and document suboptimal performance, particularly for research-oriented purposes and thereby quality control, as well as performance documentation for the above noted special purposes in the normal subject.

Biological feedback training (biofeedback training) refers to the art of sensing usually unrecognized body physiologic functions with suitable transducers, and displaying these functions by suitable means in order that the patient may be made aware immediately of body function performance. Through this technique, the patient interacts with a displayed signal to optimize the body function. Many patients can become aware of otherwise unobserved body function, and often learn to influence favorably these functions in a relatively rapid training period. Of particular effectiveness and value is so-called "primary reinforcement", (herein described as "positive" biofeedback) wherein a basic body function is used as part of the stimulus to biofeedback training. Dyspnea relief with efficient breathing patterns would be a type of primary reinforcement biofeedback training.

SUMMARY OF THE INVENTION

A unique and economical way suitable for home application or sophisticated hospital use has been found to provide positive biofeedback training for respiratory performance, using a system for training, evaluating, measuring, comparing and quantitative respiratory biological performance. This system functions to measure air flow through natural passages, and to generate a signal representative or respiratory bidirectional air flow. A circuit is provided for integrating the flow signal with relation to a time base to produce an integrated volumetric signal and for comparing the integrated signal in real time with predetermined desirable values on the time base, according to a prescribed waveform, by detecting initiation of inspiration to trigger an ideal time cycle display of respiratory breathing volumes. The system includes feedback means for visually displaying the real time measured valve and predetermined desired value, superimposed in different observation modes simultaneously on a cyclic display video screen displayed on a time-repetitive respiratory signal.

Accordingly, it is an object of the present invention to provide a system for sensing and displaying in real time a variable analog function representative of a sensed respiratory biological condition for visual comparison with a desired predetermined analog function representative of a prescribed altered condition. This system includes means for generating an analog signal representative of the variable analog function as a waveform, display means having scanning means with a predetermined time frame, first memory means of storing the predetermined analog waveform, second memory means for storing said predetermined analog function as a waveform, means for sensing the biological condition as an analog function for storage in said second memory means, means for reading out each of said first and second memories in timed relation to the scan of said display means; and means for generating a display in said display means when a value read out from either of said first and second memories corresponds to a current scanned position of said display means.

In the system each of the first and second memories are digital memories known in the art as ROM (read only memory) or RAM (random access memory), and the first memory stores sample values of the predetermined analog waveform. The system also includes means for sensing the biological condition, including means for integrating the sensed analog signal and means for generating digital sample values of the integrated signal at a time rate synchronized with the line rate of scan of the display means.

A multiplexing device is provided for storing successive digital sample values in corresponding successive storage positions of the second memory means at a first rate related to the cycle time of the variable analog function and for reading out digital values in alternating succession from each of the first and second memory means at a second rate related to the rate of scanning each successive line of the display means, and a counter means is provided for accumulating a count corresponding to the number of lines scanned in a given raster scan of said display means.

A comparator is provided for comparing the digital value read from either of said first and second memories under control of the multiplexer with the line count of said line counter for producing a video display output signal when said digital line count corresponds to the digital value read from said memory.

A further object of the present invention is to provide a first digital-to-analog converter for converting the digital value of the standard waveform read from the first memory to a corresponding analog signal and a second digital-to-analog converter for converting the digital sample values of the variable analog waveform read from the second memory. These D/A converters function with first comparator means for producing an output representing a predetermined difference between the analog outputs of the first and second digital-to-analog converters.

Another object is to provide a mixer for receiving the video output of the comparator and the line and frame signals for generating an output television signal for supply to a standard television display.

The system is advantageous in that real time performance may be superimposed visually on an ideal display, and a phantom line technique may be employed for quality control, data storage and analysis. The flow signals may be utilized with pressure sensing means and biofeedback, including variable orifice devices for breathing.

These and other objects and features of the invention will be seen in the following description and in the drawing.

THE DRAWING

FIG. 1 is a schematic diagram of an electronic system for a pulmonary TV display;

FIG. 1a is a modified diagram showing manual overrides;

FIG. 1b is a schematic diagram of an alternative blinker display;

FIG. 5 is a schematic representation showing the biofeedback display in combination with a pneumatic device and pressure equipment.

DESCRIPTION OF PREFERRED EMBODIMENTS

Figure 2:
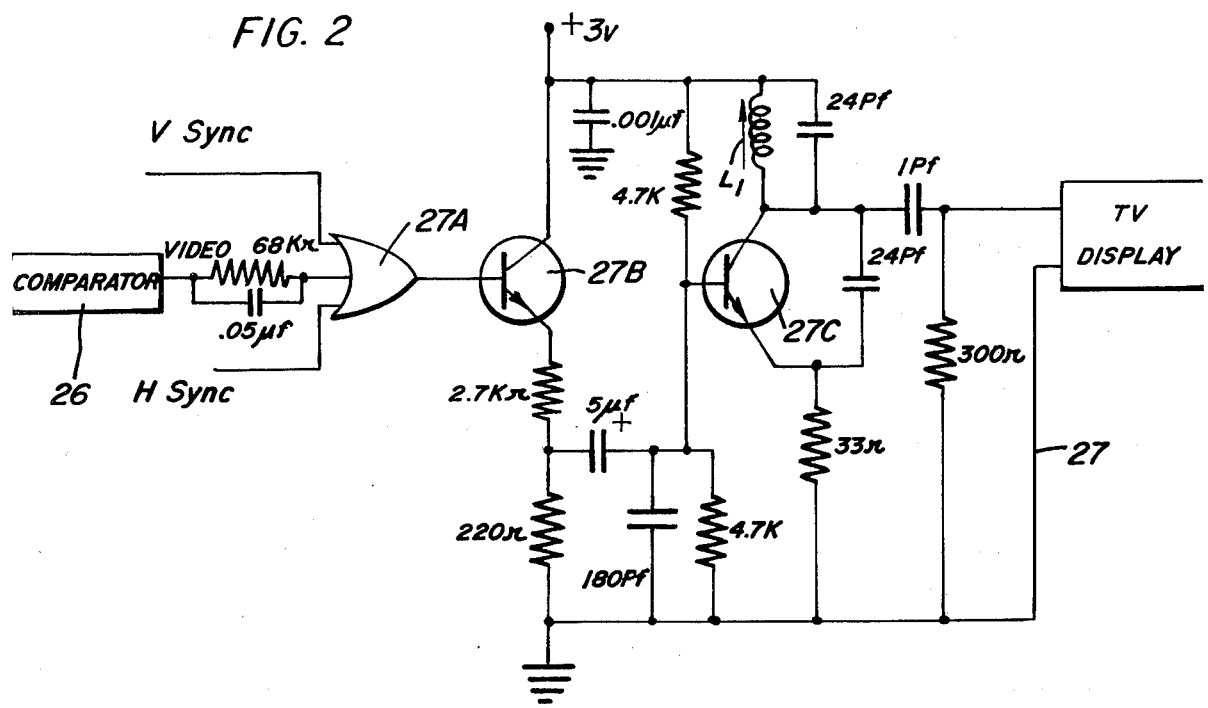
FIG. 2 is a circuit diagram of a portion of the system shown in FIG. 1.

In the following description, metric units are employed unless otherwise stated. Particular attention is directed toward the treatment of human patients having pulmonary disorders. The underlying concept relates to the display of optimized breathing patterns on a suitable visual device. In the preferred embodiments, a real time breathing pattern is generated by the patient and superimposed on the display in order that the patient is encouraged to correct his own patterns and perform them in a manner of optimum breathing efficiency. So-called "biofeedback" assistive training enhances the efficiency of breathing or mechanical assistive breathing programs. In another mode of operation, error parameters are defined about the optimized breathing pattern, with suitable audio/visual display, alarm, or recording of efficient patient performance for training, quality control, and research purposes.

It is well known in the art, that mechanical active breathing and aerosol/dust delivery to the lung is a complex maneuver, particularly so in patients with deranged lung function, which occur secondary to a variety of disease processes. As such, a complex and unique breathing pattern may be needed to solve the mechanical assistive problems of the individual patient.

This invention is a breathing training system, with a series of mutually compatible devices, depending upon the particular patient, physician, or researcher needs, all based on the Primary Reinforcement Biologic Feedback Training concept. The primary device is a sophisticated adjustable apparatus that allows for independent adjustment or respiratory rate, inspiration:expiration ratio, tidal volume, and respiration airflow waveforms. The desirable or prescribed waveform pattern may be displayed visually by appropriate means such as an oscilloscope, television screen, or the like, in the form of an interrupted line. The vertical ordinate is calibrated as to volume, and the horizontal abscissa is calibrated relative to time parameters. Accordingly, the volume/time (flow) waveform pattern is a separate variable that may be programmed within these constraints to provide an optimized inspiration and expiration airflow pattern relative to time and volume. The patient breaths through a suitable transducer that senses airflow. At the beginning of patient inspiration, a suitable reset trigger senses inspiratory airflow, cancels the previous cyclic display, and initiates the programmed waveform for display and comparison. The inspiratory and expiratory airflow into and out of the patient is sensed by suitable transducers, electronically integrated into a calibrated tidal volume signal relative to time, and multiplex displayed on the visual display. Typically, the patient is encouraged to have his real time performance solid line display follow the ideal interrupted line program, essentially overlying and obliterating the programmed interrupted line. Inadequate patient performance can immediately be seen in a qualitative and quantitative manner in real time, and the patient thereby is encouraged in a positive manner to correct his deficient performance. The passive versus muscular active phase of expiration may be indicated by suitable signals on the video display, or the control consol, for example a green light for the passive phase, and a red light for the active phase. Suitable adjustments control the time switching from active to passive phases. In the condition known as "dynamic bronchial compression" (DBC) the intrathoracic airways are subjected to compression. As the chest becomes smaller on expiration, thereby squeezing the alveolar structures to force them to move air down the bronchial tubes to the outside, the bronchial tubes are also compressed somewhat. This bronchial tube compression narrows the tubes, and thus produces a counter productive situation wherein undesirable resistance to expiratory airflow is developed during the act of expiration.

In some clinical situations, notably emphysema, this is a particularly serious mechanical constraint. Loss of normal lung elastic recoil in this common disease, predisposes the airways to premature and severe collapse, thus trapping air within the lung. In some cases, more forceful expiration only compresses the airways further without evacuating air and producing an exhausting and distressing impairment to breathing. It should be apparent from above that there is a subtle and critical dynamic balance between the need to actively and passively exhale gas from the lungs in order to minimize this critical dynamic closing pressure. One method sometimes used to counteract this undesirable premature airway closure is so-called "Pursed Lip Breathing". Here the patient is taught to provide a slight degree of expiratory retardation by partially closing (pursing) his lips on exhalation, This causes the airway pressure to become slightly relatively positive, thereby by slight airway backpressure counteracting the compressing force from the chest wall which is compressing the airways, and thereby tending to keep the airway open. This may be a counter-productive act of expiration, as excessive retardation through lips too tightly constricted can become a dominant force limiting expiratory air flow. Therefore, this is another subtle and difficult mechanical constraint for the patient to master.

Should the physician or respiratory therapist instructing the patient recognize programmed inadequacies, the various parameters can be independantly and easily changed to an optimum for various different needs. For example, basic quiet breathing, exercise, control of acute shortness of breath situations or the different patterns required with respiratory assistive devices, aerosol delivery, dust delivery, or the like. In essence, this would be the definition of a mechanical medical prescription similar to the familiar medical drug prescription ordered by a physician. The desirable parameters can then be programmed into a simple and economical device for use in the patient's home to be duplicated on a suitable display, such as a television screen, kinescope, cathode ray tube, liquid crystal display, etc, in an economical manner. This enhances a clinical training program and assures the patient does not revert to undesirable breathing patterns by reinforcing the personally supervised clinical treatment prescription.

The patient-monitoring device described hereinafter is an analog-to-digital system for achieving time correlation between a programmed breathing cycle and patient performance. This apparatus provides a display of these functions essentially simultaneously in so far as the human observer is able to distinguish. Although time lags may be easily distinquished by electronic means, the visually discernable display is usually simultaneous with the waveforms being temporally and spatially coordinated.

The circuitry in the block diagram of FIG. 1 shows preferred methods and apparatus for showing certain pulmonary funtions of volume/time (flow) on a TV kinescope display. These functions are tidal volume, respiratory rate, inspiration/expiration ratio, inspiration waveform, expiration waveform and muscle passive/active time. The device is useful for clinical analysis of the breathing patterns of a human and also can be applicable to home use by a patient for biofeedback training purposes and breathing monitoring. The device is designed so that various waveforms representing the ideal breathing patterns can be selected and displayed on a TV screen. The data for these waveforms are stored in three read only memories (ROM). The main ROM 32 contains the timing/ratio wave, an inspiration ROM 34, and an expiration ROM 33. By front panel switches, 8,9 various combinations of these data can be selected. The resultant figure on the TV screen is the ideal waveform selected by the operator or physician.

To obtain the respiration performance waveform, a person breaths through a flowmeter 1. The flow of the air is detected by a transducer 2 which produces voltage corresponding to the amount of airflow. The output transducer 2 is amplified and filtered in the low pass active filter 3. When this voltage exceeds the reference voltage of the comparator 4, a signal output causes the one shot 6 to fire. The length of the output of one shot 6 is equal to one TV frame. The one shot provides a start of inspiration pulse which resets the integrator 5, the data counter 12, enables the random access memory (RAM) 18 through the "or" gate 19 and causes the multiplexer 17, (for example, Texas Instruments Inc. Type SN 74157) to feed blanks as data into the RAM. The output of the one shot delay 35 causes 18 to write blanks into all locations. At the end of the start of inspiration pulse from the one shot 6, the integrator 5 starts integrating the signal from the amplifier 3. The output of the integrator is input into the analog-to-digital (A/D) converter 14. The analog-to-digital convertor convers at a rate prescribed by the variable rate oscillator 13 which is preset from the front panel by a physician or operator. The digital information is now presented as data to the input of a random access memory (RAM) 18 through the multiplexer 17. The data conter 12 increments at end of convert pulse which also is input to the or gate 15 causing the address multiplexer 16 (for example Texas Instruments Type SN 74157) to change state. The address multiplexer 16 now outputs the data counter contents as the address to the RAM, thus the data is entered into the correct address in the RAM 18. Because the data is written to the RAM infrequently compared to the read rate, it will not be noticed on the TV screen. The data collected during breathing is stored in a random access memory and then displayed on the screen. Limits for the comparison between the patient data and ideal waveform can be established by the operator on the front panel. The difference between the ideal and the patient data is easily seen on the screen and any deviations greater than the error selected by the physician, can be stored in an appropriate memory and then analyzed by an external computer. When the line counter output and the output of the memories agree in the comparator 26, a video signal is provided to the mixer which then causes a dot to be written on the TV screen. The data counter 12 provides the addresses for writing data to the RAM when the muliplexer is in the alternate state. Since there are 256 possible addresses for each display, there will be 256 possible times that the output from the ROM or the RAM could agree with the line counter in the comparator and cause a video signal on the TV screen. Thus every line has 256 possible dots as the waveforms are generated on the TV screen.

From the preceeding description it can be seen that the 256 address words define the column with respect to the left (start-of-inspiration) side of the TV screen, and that the sampled data provides the vertical position on the screen. Accordingly, this information is used on the TV screen for horizontal and vertical location and can be used by the data collector in the same way to analyze the information input from output device 39. Device 39 is a data collecting interface (DCI) designed from readily available integrated circuits, circuit components selected depend to a large extent on system architecture, component/subcomponent interrelationship and functioning of the data collector. However, in all cases the data collected in the interface is the address and patient data of each sample, which deviates from the norm. The boundary of the normal data is stored in the ROM's. In addition, the start of inspiration (breath) pulse from the one shot 6 is counted in the interface and output to the data collector. Thus a block of addresses and data samples transmitted to the data collector between breaths are known to have occured during the breath with the lowest number adjacent to the block. This would assure blocks of data being stored with the appropriate breath in correct sequence.

The means of determining when sampled patient data has deviated from the norm is by comparing in the interface the RAM 18 data input to the ROM 32, 33, 34 data obtained at address 30 output. When the data deviates outside the norm, the data with its address, both which are obtained at the input to the RAM (18) is strobed into the interface as as result of the comparison. When the interface contains error data it indicates to the data collector that information is ready to be transferred.

Another way to obtain error data is shown in FIG. 1. When a comparison between the patient data and the normal data from the ROMs indicates an error, a pulse occurs at the output of the comparator 44 and strobes the data from the output of the RAM 18 and the address at the RAM 18 input into the interface 39 for transfer to the data collector.

The data collector may be any device capable of storing large amounts of data. Applicable devices would include but not be limited to large scale computers, minicomputers, microprocessors, and digital magnetic tape units.

The device ultimately used to process the patient data would contain in memory a duplication of normal breath boundaries, together with the address of each boundry point. The data might be a direct duplication of the ROM's 32, 33, 34 or the same information stored according to the requirements of the performance evaluation software.

The passive/active position switches 40 are decoded at 42. This signal and a decoded address from 41 are input to an "and" gate 43. With coincidence of the two signals, the green passive light switches to a red active light indicating that the patient should start active expiration breathing. Thus the operator selects the addresses from the front panel at which he wants the active light to occur and the patient to start active breathing. When the addresses from multiplexer 16 increments to that point and there is an error indicating the active breathing has not started, then the light becomes red. When the error is below the selected amount, the light will turn green again.

The ideal waveform is generated by adding the waveforms from the ratio ROM 32, expiration ROM 33, and inspiration ROM 34. Each of these blocks can contain more than one eight-bit ROM. The number of ROM's stacked will depend on the number of different waveforms desired. The waveform selection switches for ratio, inspiration and expiration vary the higher order address bits of the respective ROMs to select different waveforms. The lower order address bits address the data to be displayed on the TV screen. The data out of ROM's 33 and 34 are added together in item 31, an eight bit adder, and that output is then added with the ouput of 32 in the adder 30, an eight bit adder. Element 29 represents eight tristate buffers which enable the ideal wave data to feed into the comparator 26. The output of the adder 30 is also input into a digital-toanalog convertor (D/A), 38. The output of D/A converter 38 is input into a comparator 24. This comparator provides comparison against the patient data which has been digital-to-analog (D/A) converted in 22 so that the comparator 24 can be adjusted to provide an error margin selected from the front panel by a physician. Comparator 44 has a different error margin, generally smaller, which can also be selected from the front panel by the physician. Limits on comparator 44 may be 5% to 10%, while comparator 24 may be 15% to 25%.

The 4.1 megahertz oscillator 7, has been selected to provide signals compatible with a standard television's horizontal and vertical signals. The output of the oscillator is counted and divided by N in the counter 10. This counter provides an enable signal every Nth column, causing a dashed line representing the ideal waveform to be displayed on the TV screen. The output of the oscillator is also counted by a column counter 11 to provide addresses for the ROM through the multiplexer 16. When the column counter counts 256 bits, it overflows and resets. The overflow signal provides a horizontal sync for the TV modulator and increments the line counter 28.

The means for detecting of initial inspiration serves as a reset function and to synchronize the readout of the ideal waveform from the ROM's as well as the read in and read out of data from the RAM for the sensed respiration cycle. The sensed respiration is integrated and converted to digital form by A/D convertor 14 and supplied through a data multiplexer 17 to read the data samples into the RAM at the approriate rate and thus into the appropriate storage position. Multiplexer 16, on the other hand, serves alternately to readout data from the ROM's or from the RAM. The rate of readout is a function of the column counter and thus of the display, so that 256 dots are generated for each of the two waveforms in a typical TV display.

Several comparators are used in the circuit, however, multi-function comparators may be employed on a time-sharing basis. Comparator 26 is used for the display function. Here, the line counter 28 (responding to the lines of the raster and thus the height along the raster) supplies a count up to comparator 26 corresponding to the physical position of the scanning beam on the CRT screen. Depending on the current state of the multiplexer, one or the other of the digital words read out from the ROM or the RAM, and which is simultaneously presented to the comparator 26, provides the data input which is compared with the current CRT scanning beam position by comparator 26 which then either generates a video display signal or no signal. Since the ROM and the RAM readouts are performed in a timeshared (i.e., multiplex) manner, and since in real time the beam of the CRT is only at one position at a given instant, it will be seen that there is a time sequence of the video outputs even where the sensed breathing curve is in fact identical with the ideal curve — although this time differential would be so small that it would not be visually noticeable.

Comparators 24 and 44 relate to the function of determining the degree of compliance of the sensed breathing curve with the ideal curve and provide appropriate alarm and/or recording outputs when those limits are exceeded.

Erratic breathing patterns by the subject may make it difficult to properly initiate the desirable waveform breathing pattern. In such cases, it may be desirable to reset the cycle manually instead of by detecting inspiration flow. An inspiration override switching device allows a technician or operator to interact with the patient and the system to integrate patient needs properly into desirable machine generated performance parameters. Once initiated, the subject patient would then better be able to relate to the desirable breathing patterns. Referring to FIG. 1a, a modification of the system of FIG. 1 is shown which incorporates manual override subsystems. This manual override device could take two forms. The first would be the display of individual single breathing patterns in the usual mode of operation. The start of inspiration pulse output by the one shot 6 can be parallelled by a switch which will also give a start of inspiration pulse. The start of inspiration pulse resets the integrator 5 and thereafter the operation is as described for FIG. 1. This allows the operator control of the start of the display to coincide with the start of breathing of the patient.

A second approach might be to display a series of breathing patterns in a prescribed program. For example, in the series of breathing patterns required by the Lamaze obstetrical method, at the beginning of a labor pain, the patient could press the manual override switch and initiate a program of multiple breaths in multiple ways in individual breaths to achieve a desired obstetrical breathing pattern. The multiple breath display would require only an additional logic which would not depart from the scope of this invention. The expiration portion of the cycle may also be provided with manual override switch by modifying the circuit of FIG. 1 to actuate counters 10, 11 manually. By activating this switch, the output of oscillator 7 is interrupted and whatever display is presented at that time will be preserved in the display without progression.

Ideal breathing patterns of necessity require the patient be in a stable state in order to utilize said optimize breathing patterns. This would imply previous unstable states, such as chest overinflation known commonly in the art as "airtrapping" be initially obviated. This is so because the act of expiration in emphysema patients is more difficult than the act of inspiration, thus promoting a perpetual state of airtrapping overinflation. To come from a state of airtrapping overinflation to one of relative normal chest volume, the manual inspiration override program might be initiated. Also, the same result could be obtained by activation of a manual expiration override switch which could be utilized in two formats. The first would be a simple manual override switch 7A which would delay the beginning of the video display of the next cycle, during which time the patient would be instructed to continue the act of exhalation, thereby emptying his chest of undesirable volumes of air prior to initiation of next inspiration. In a second mode of operation, utilizing a simple timing delay device, the active exhalation could be prolonged for a prescribed period of time, for example 2, 3, or 4 seconds per superimposed cycle of prolonged expiration and thereby delayed inspiration time of the next cycle. This modification is also shown in FIG. 1a.

The timer could be activated by a manual switch, as described, or automatically from a simple end of expiration timing means.

A manual override on expiration can be accomplished by disabling oscillator 7 into the column counter 11. This will allow the operator to stop the display while the patient continues breathing out or at any point in the cycle. To avoid stray pulses due to bouncing of a switch, a gated amplifier can be inserted in series with the output of oscillator 7. The gate of the amplifier can be controlled by a set - reset flipflop, which in turn is controlled by a manual switch and clocked by the output oscillator itself.

Real time performance deficiencies will be indicated by departure of a solid performance line from a broken desirable parameter line. In an alternative embodiment of the video incentive positive biofeedback display, the broken line display of ideal performance is enhanced by a progressive real time optical blinking display. The display of the dotted or broken ideal performance curve is enhanced in biofeedback modes by making the stationary dotted display blink progressively in real time sequentially along the programed dotted display of a stationary type. This would more precisely enhance the positive biofeedback mode of operation. A representative blinking display is shown in FIG. 4j. The real time position indicator circuitry for blinking dot display can be obtained by modifying the circuitry of FIG. 1 as shown in FIG. 1b. The blink position is kept just leading the real time data. Its position is determined by adding one count to the data counter in the data plus 1 counter 12A. Each bit of the data plus one counter 12A and the address from the multiplexer 16 are input to a decoder 12B. The decoder contains an inverted exclusive OR for each bit of the address. The output of each of these is input to an AND circuit. When there is coincidence on all lines of the AN circuit, gated oscillator 12C is gated on by the output from decoder 12B. The output of oscillator 12C alternately inhibits and enables the inverter 20. This will inhibit the input, causing the video to turn off for several frames and on for several frames. The frequency may be selected to provide an optimum blinking rate. The video output of comparator 26 is utilized in a modulator oscillator mixer circuit which feeds the TV display.

Referring now to FIG. 2, the vertical and horizontal synch signals are fed with the comparator video output to a NOR gate 27A (Motorola MC792P). All inputs are TTL level. The NOR gate output is connected to the base of an NPN-type transistor 27B. The circuit is shown with preferred values of resistance and capacitance. Transistors 27B and 27C may be type 2N3904. Variable inductance L, may be constructed with 4 turns of No. 18 copper wire spaced about 1 cm on about ½ cm diameter slug-tuned form. This circuit is designed to operatively connect to the 300 $\pi$ twin lead to a standard television set.

FIG. 2 is a standard circuit for connecting digital data to a television set. It can easily be replaced by other commercially available systems which require horizontal and vertical synchronized video inputs to input data to a TV set.

The visual display may be any dynamic electro-optic device capable of accepting the pulmonary program and patient data on a real time basis. For purposes of simplicity, emphasis is placed on the kinescopic display adaptable for use with a standard television receiver set. The rectilinear raster scanning systems are commercially available and are advantageous for use with the present invention with little or no modification. The typical raster scanning circuits can be easily adapted for interfacing with the present data input.

Various modifications of the display device are feasible, including electrically-activated grids, such as those employing liquid crystal elements. While the preferred displays are conventional, with time on the abscissa (horizontal axis) reading left to right respiratory volume being shown on the ordinate (vertical axis), other visually discernable displays are contemplated, for instance, a circular CRT display with expanding circles for the prescribed volume and measured flow conditions.

Various optional equipment may be employed as part of the invention. In training emphysema patients, dynamic bronchial compression may be overcome by achieving a "pursed lip effect". In this technique a variable outlet orifice can be employed with the mouthpiece to obtain a constant back pressure, which minimizes this form of bronchial compression.

As a further embodiment to evaluate and quantitate patient performance, mainly for quality control and research purposes, an additional device can be adapted in convenient modular fashion into the basic units. This optional equipment defines phantom confidence limits parallel to and above and below the desirable waveform, for example positive and negative 10% and 25% limits. These may be "phantom" waveforms parallel to the desired waveform. When patient performance exceeds the confidence limits, this is electronically sensed in the appropriate volume/time relationship. If desired, this can initiate a visual and/or auditory alarm of inadequate performance to further alert the patient and encourage him to better performance. The type and magnitude of said confidence limit excess can be transmitted outside for data storage and/or data processing means in order to gain comprehensive insight into patient performance with either spontaneous breathing and/or breathing assistive waveform patterns.

Figure 3:
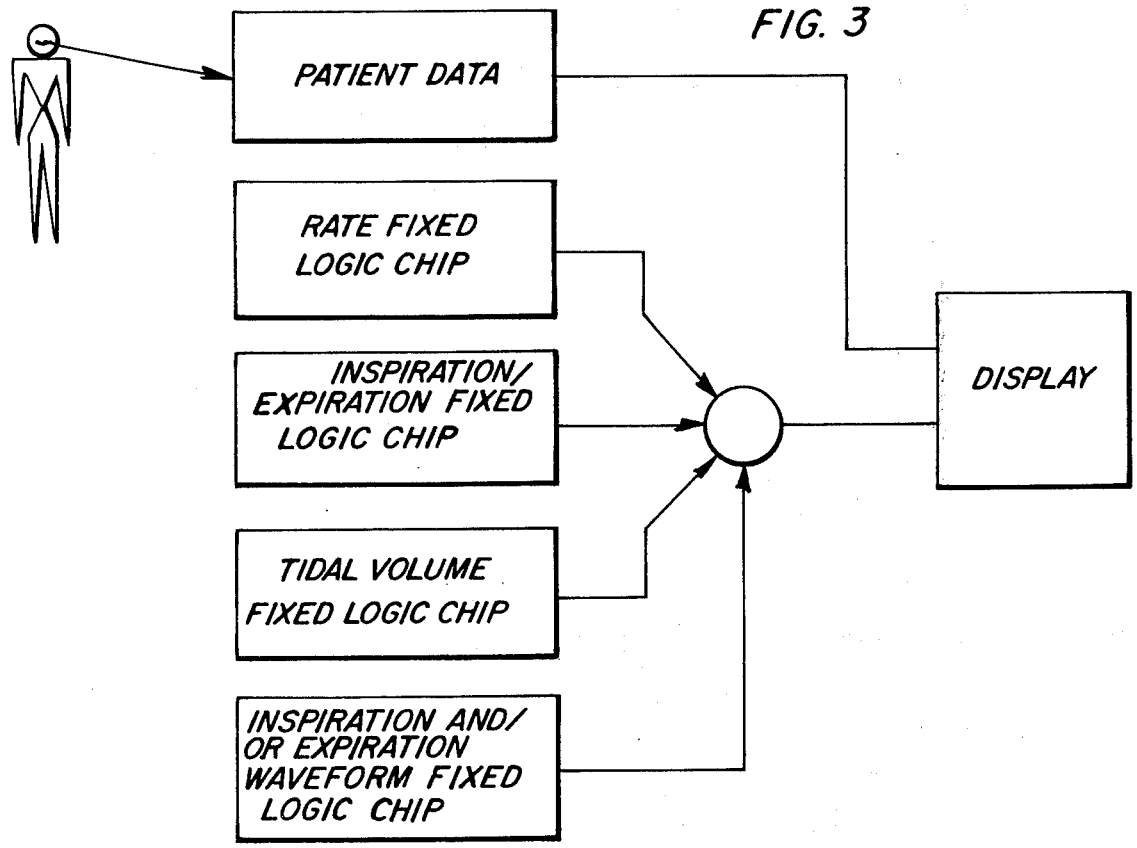
FIG. 3 is a block diagram of a typical simplified device using fixed logic circuits.

The ideal pattern may be pre-set by selecting a circuit board or special memory chip integrated circuit or the like, having the desired values of tidal volume, respiratory rate, etc. These may be economical fixed values in the selected simple circuit, as shown in FIG. 3, or the system may be alternately provided with complex means for adjusting the ideal parameters over wide ranges. For instance, the tidal volume may be varied from 0 to 5,000 cc, while the basic respiratory rate can be set from 0 to 40 cycles per minute and the inspiration/expiration ratio may be varied from 1:1 to 1:10 all with variable adjustable waveforms. These are substantially wider than would ordinarily be used and provide for extreme patterns, if desired. Various linear and non-linear waveforms may be selected for inspiration and exhalation of air and a terminal inspiration plateau hold pattern may be selected at 10 to 50% of the terminal basic inspiration timing. The breathing muscular passive/active time indicator for expiration may be preset for 10 to 50% of terminal exhalation or switched out of the circuit.

Noise suppression and curve smoothing circuits may be switched into the flow measuring circuit, typically between the transducer/amplifier and the flow integrator. If a matrix memory is employed for storing the waveform, the outputs of memories can serve as direct addresses to the display. In a typical matrix-selection display, timing control of readout is required, but the circuitry can be greatly simplified by prefixed logic chips to incorporate an economical TV raster scanning display, or without departing from the scope of this invention may utilize standard displays of many types with additional complex electronic circuitry to display both horizontal and vertical axis parameters.

The display may be supplemented by other kinescopic units, data recorders and processors linked to adjustable error limit performance parameters or on-line oscilloscope and the like. Pulmonary pressure indicating or recording devices may also be added, coupled to variable expiratory orifice apparatus to coordinate exhalation flows to desirable exhalation pulmonary pressures.

In some situations, it may be desirable to have plural programs which can be selected or changed quickly by a manual switch. For instance, a first fixed program could provide a regular breathing program, with a second fixed program for exercise breathing or acute dyspnea and a third fixed program for use with breathing assistive devices. An exterior selector switch would permit the operator to change the program instantly.

Figure 4A:
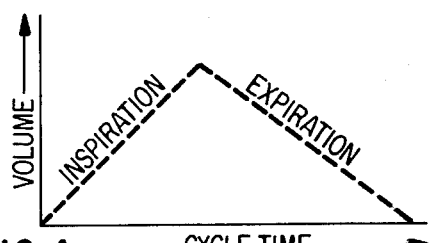
FIGS. 4a to 4j are graphs representing typical retilinear displays of tidal volume and time for various ideal and performance curves.
Figure 4B:
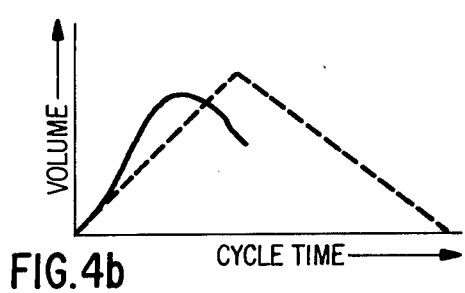
Figure 4C:
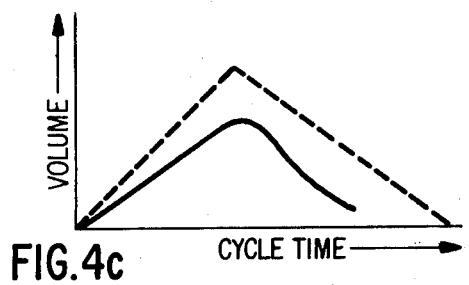
Figure 4D:
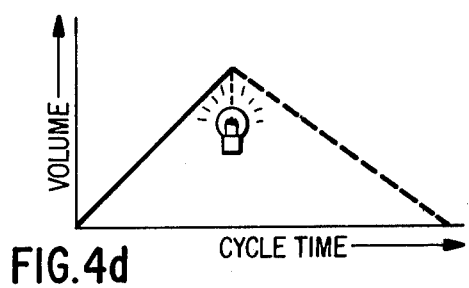
Figure 4E:
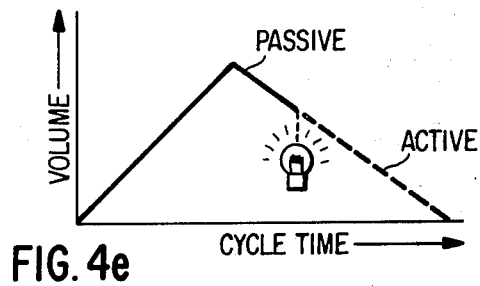
Figure 4F:
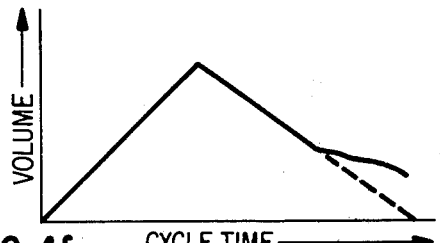
Figure 4G:
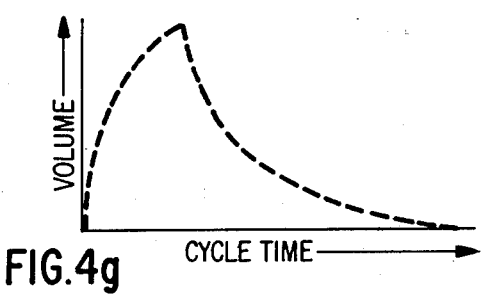
Figure 4H:
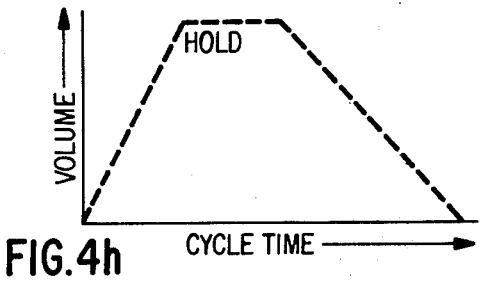
Figure 4I:
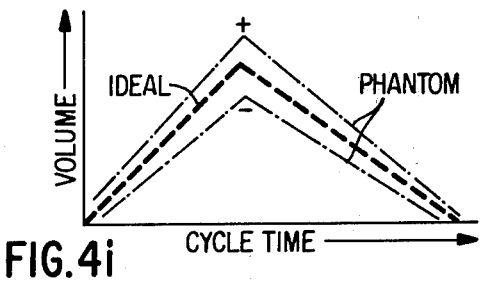
Figure 4J:
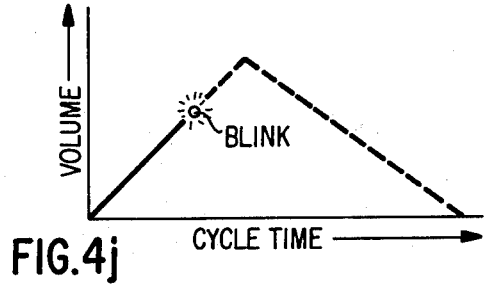

In FIG. 4a to 4j, typical displays are shown, using rectilinear coordinates. The ideal pattern or prescribed tidal volume/time relationship is depicted as a broken line. In FIG. 4a, the ideal pattern has an upwardly sloping inspiration curve up to the maximum tidal volume to be taken into the lungs. A typical expiration curve is also shown.

FIG. 4b shows an unsuccessful attempt wherein the solid performance line indicates the integrated flow is too fast and desired tidal inspiration volume is not achieved. In FIG. 4c, the slow inspiration performance curve shown in solid line indicates the inspiration flow is too slow and the desired maximum volume has not been achieved before expiration begins.

FIGS. 4d and 4E show a successful performance wherein the broken ideal pattern is matched by the superimposed performance curve, resulting in a first visual signal (e.g.-green) to indicate the beginning of the chest elastic recoil passive expiration period and a second visual signal (e.g.-red) to begin muscular active expiration. FIG. 4f shows a common deviation from the ideal, wherein the patient does not achieve total expiration volume within the required time, and inadequate terminal expiratory flow rates.

The inspiration/expiration time ratio and flow waveforms of inspiration and expiration can all be independently adjusted. FIG. 4g shows a short inspiration, long expiration time ratio, each with a different waveform.

FIG. 4h shows a typical inspiration hold pattern, with a plateau hold at terminal inspiration. FIG. 4i shows a typical visible ideal curve display with ± phantom lines. The modification to provide a leading blink indicator is shown in FIG. 4j, corresponding to the embodiment of FIG. 1b.

The above-described system may be modified by substitution of various components or additional equipment. Various flow transducers are adaptable for use with the present system. In addition to the deflective reed type of transducer, those devices operating on differential pressure meansurements, hot wire anemometers, or pitot tubes may be employed. The typical flow transducer can be easily adapted for measuring air flow in natural passages with a suitable mounthpiece or mask.

Biofeedback of tidal volume may be combined with other sensed conditions, especially pressure measurements, as shown in FIG. 5. A patient or trainee breaths through a flow transducer 1 operatively connected between a mask or mouthpiece and a pneumatic device. The flow transducer provides the input to the biofeedback display system and a separate pressure transducer 50 is provided as a means for measuring air pressure between the subject and the pneumatic device. This may be an indicating mechanical pressure gauge, bellows, or electro-mechanical detector. Pressure parameters can be established separately from tidal volume; however, means may be provided for concurrent display of an ideal pressure pattern with the tidal volume display. Means for generating a signal representative of respiratory pressure (e.g. piezoelectric crystal) may be input to a comparator circuit to determine performance relative to a predetermined or ideal pressure pattern. Suitable alarms and data acquistition devices may be attached.

The pressure measuring system may be employed in conjunction with various pneumatic devices including breathing assistive devices such as an intermittant positive pressure breathing device or an aerosol or particle deposition device. For breathing training, the combined tidal volume and pressure system is valuable for use with a Lamaze-type obstetrical breathing controller, a scuba diving teaching device, or a musical wind instrument. A pulmonary function testing station may also be employed in conjunction with the present system.

A flow restricting and/or pressure control device can be connected between the patient and the flow transducer. In some cases it is desirable to keep the pressure constant or at a predetermined dynamic value despite variations in flow/volume delivery from the patient. For such results a variable orifice may be employed. Such apparatus may include an adjustable-opening iris or sliding vane valve to give the desired breathing patterns. Such optional apparatus can be used with a pursed lip breathing trainer, which usually employs a transducer to measure pressure built-up against a flow restrictor.

This invention has been described with digital electronic logic means to take presently available electronics. Also, this concept may be implemented in a high speed digital computer, in standard CRT computer and/or microproscessor display means. This concept may be implemented by microprocessor means. The limiting factor on presently available microproscessor means is the required speed of pulse recognition and processing required to interact effectively with standard high speed television raster scanner devices. Future electronic development may see the creation of microproscessor devices with sufficient interactive pulse recognition and proscessing speed that microproscessor implementation will become technically and economically effective. The inventive concept is intended to embrace such microproscessors as they will only be another means of implementing the invention.

While the invention has been explained by particular examples in the specification and drawing, there is no intent to limit the inventive concept except as set forth in the following claims.

What is claimed is:

1. A system for measuring and displaying real time respiratory air flow in relation to an optimized air flow, comprising:

means for measuring the respiratory air flow and for generating a signal representative of instantaneous volumetric flow rate;

means for displaying each of said measured respiratory air flow and said optimized air flow curve with respect to a time base and spatial relationship pre-established in connection with said optimized air flow curve;

means for sampling said integrated respiratory air flow signal to produce integrated sample values thereof in accordance with said pre-established time base and storing said integrated sample values in a second memory;

means for storing sample values of said optimized air flow curve as a standard waveform in a first memory;

means for reading out successive values of said standard waveform from said first memory and of said integrated sample values from said second memory, in sequence for each of said memories and at a rate synchronized with the rate of scan of said display means; and means for comparing the position of the scanning beam of said display means with the values read out from each of said first and second memories for generating a video display signal when a value read from one of said memories corresponds with the position of the scanning beam, thereby to produce a display of that value on said display means.

2. The system of claim 1 further comprising means for sensing initiation of respiratory inspiration and resetting read out of said first memory to correlate sampling of sample values from said respiratory air flow signal.

3. The system of claim 2 further comprising electronic means for storing the sample values in digital pattern form.

4. A system for sensing and displaying in real time a variable analog function representative of a sensed biological condition for visual comparison with a related predetermined analog function representative of an optimal prescribed condition, comprising:

means for generating an analog signal representative of the variable anolog function;

display means having scanning means with a predetermined frame time;

said display means comprising a scanning type display means having a predetermined scan raster and frame;

first memory means for storing said predetermined analog function as a waveform;

second memory means for digitally storing said variable analog function as a waveform;

means for sensing said condition as an analog function and providing digital signals representative of the analog function for storage in said second memory means;

means for reading out each of said first and second memories in timed relation to the scan of said display means, and means for generating a display in said display means when a value read out from either of said first and second memories corresponds to a current scanned position of said display means.

5. The system of claim 4 wherein each of said first and second memories comprise digital memories, said first memory storing digital sample values of said predetermined analog waveform; and said means of sensing said condition including means for integrating said sensed analog signal and means for generating digital sample values of said integrated signal at a time rate synchronized with the line rate of scan of said display means.

6. The system of claim 5 further comprising:

multiplexing means for storing successive digital sample values in corresponding successive storage positions of said second memory means at a first rate related to the cycle time of said variable analog function and for reading out digital values in alternating succession from each of said first and second memory means at a second rate related to the rate of scanning each successive line of said display means;

counter means for accumulating a count corresponding to the number of lines scanned in a given raster scan of said display means; and comparator means for comparing the digital value read from either of said first and second memories under control of said multiplexer with the line count of said line counter for producing a video display output signal when said digital line count corresponds to said digital value read from said memory.

7. The system of claim 6 further comprising:

a first digital-to-analog converter for converting the digital value of said standard waveform read from said first memory to a corresponding analog signal;

a second digital-to-analog converter for converting the digital sample values of said variable analog waveform read from said second memory; and first comparator means for producing an output representing a predetermined difference between the said analog outputs of said first and second digital-to-analog converters.

8. The system of claim 4 wherein there is further provided a mixer for receiving the video output of said comparator and said line and frame signals for generating an output television signal for supply to a television display.

9. The system of claim 4 wherein said first memory includes a digital read only memory and said second memory includes a digital random access memory.

10. A real time biological performance evaluation and testing device which comprises:

means for measuring respiratory air flow and generating a flow signal representative of said air flow;

means for integrating said air flow signal with relation to a time base and generating a volumetric signal representative of the integrated air flow;

means for detecting initiation of inspiration and resetting an ideal volumetric respiration pattern;

means for comparing the volumetric signal with the ideal volumetric respiration pattern signal correlated with inspiration reset; and means for visually displaying the volumetric signal and ideal pattern in visually discernible superimposed observation modes on a dynamic display.

11. A device according to claim 10 further comprising means for presetting performance error limits and providing a performance deficiency signal.

12. A device according to claim 11 comprising means for displaying the ideal pattern as a blinking spot leading the volumetric signal display.

13. The device of claim 10 comprising means for superimposing the volumetric signal and ideal pattern on the display.

14. A device according to claim 10 further comprising means for measuring respiratory pressure and generating a pressure signal, means for comparing the pressure signal with an ideal pressure pattern signal correlated with expiration or inspiration reset, and means for displaying the pressure signal and ideal pressure pattern signal concurrently with the volumetric signal and the predetermined volumetric respiration pattern signal.

15. A device according to claim 10 further comprising means for activating an alarm in response to predetermined deviation of the volumetric signal from te ideal pattern.

16. A device according to claim 10 further comprising manual override means for resetting the ideal respiration pattern for initiating inspiration or terminating or prolonging expiration.

17. A device according to claim 10 comprising means for adjusting positive and negative error limits and means for detecting and indicating volumetric signals in relation to time parameters outside said error limits.

18. A device according to claim 10 further comprising a plurality of visual indicator display means and means for manually adjusting timing of said plurality of indicator display means, whereby passive or active effort is indicated in accordance with ideal volumetric wave form breathing patterns.

19. A training method for measuring and comparing respiration real time which comprises:
   measuring respiratory air flow and generating a flow signal representative of said air flow:
   integrating said air flow signal with relation to a time base and generating a real time volumetric signal representative of the integrated air flow;
   detecting initiation of inspiration and resetting an ideal volumetric respiration pattern;
   comparing the volumetric signal with the ideal volumetric respiration pattern signal correlated with inspiration reset; and
   visually displaying the volumetric signal and ideal pattern in visually discernible superimposed observation modes.

* * * * *

UNITED STATES PATENT OFFICE
CERTIFICATE OF CORRECTION

Patent No. 3,991,304          Dated November 9, 1976

Inventor(s) Deane Hillsman

It is certified that error appears in the above-identified patent and that said Letters Patent are hereby corrected as shown below:

Column 3, line 23, "valve" should read -- value --.

Column 4, line 44, "retilin-" should read -- rectilin- --.

Column 11, line 49, "⊓" should read -- ⌐⌐ --.

Claim 1, in column 14, after line 63, insert -- means for integrating said instantaneous volumetric flow rate signal to obtain an integrated respiratory air flow signal; --.

Signed and Sealed this

Fifth Day of September 1978

[SEAL]

Attest:

RUTH C. MASON
Attesting Officer

DONALD W. BANNER
Commissioner of Patents and Trademarks